(12) United States Patent  (10) Patent No.: US 7,581,877 B1
Zarrabian  (45) Date of Patent:  Sep. 1, 2009

(54) APPARATUS AND METHOD FOR MEASURING THE DEW POINT OF GASES USING SPECTRAL RECOGNITION OF THE CONDENSATE

(75) Inventor: Sohrab Zarrabian, 13521 Straw Bale La., Gaithersburg, MD (US) 20878

(73) Assignee: Sohrab Zarrabian, Gaithersburg, MD (US)

( * ) Notice: Subject to any disclaimer, the term of this patent is extended or adjusted under 35 U.S.C. 154(b) by 180 days.

(21) Appl. No.: 11/805,925

(22) Filed: May 25, 2007

Related U.S. Application Data

(60) Provisional application No. 60/808,222, filed on May 25, 2006.

(51) Int. Cl.
 G01N 25/02 (2006.01)
(52) U.S. Cl. .............................. 374/16; 374/18; 374/20; 73/23.2; 73/25.04
(58) Field of Classification Search ................... 374/16, 374/18, 20; 73/23.2, 25.04
See application file for complete search history.

(56) References Cited

U.S. PATENT DOCUMENTS 2,566,307 A * 9/1951 Boyle ........................... 374/18
6,926,439 B2 * 8/2005 Zlochin ........................ 374/20
2004/0042526 A1 * 3/2004 Zlochin ........................ 374/16
2004/0240515 A1 * 12/2004 Egan et al. ................... 374/120
2007/0246653 A1 * 10/2007 Zhou ........................ 250/339.1
2008/0123712 A1 * 5/2008 Zhou et al. .................... 372/55

* cited by examiner

*Primary Examiner*—Andre J Allen
(74) *Attorney, Agent, or Firm*—MaxValueIP, LLC

(57) ABSTRACT

A new method and apparatus is described for measurement of the dew point, and thus the vapor pressure of various gases and gas mixtures. In this method an optical element which is exposed to a gas atmosphere is cooled while its temperature is being monitored. At the same time an optical signal is sent through the back of the optical element. The optical signal goes through internal reflections. As soon as dew forms on the surface of the element, the optical signal will exhibit selective absorption due to the interaction of the evanescent tail of the optical signal and based on the chemical nature of the condensate. This invention can also be used to characterize condensable content of gas mixtures. The method allows for the spectral characterization and determination of the condensed vapor. It offers several advantages over existing methods.

29 Claims, 3 Drawing Sheets

APPARATUS AND METHOD FOR MEASURING THE DEW POINT OF GASES USING SPECTRAL RECOGNITION OF THE CONDENSATE

CROSS-REFERENCE TO RELATED APPLICATIONS

This application draws the benefit of earlier filed provisional application No. 60/808,222 filed on May 25, 2006.

STATEMENT REGARDING FEDERALLY SPONSORED RESEARCH

Not Applicable

THE NAMES OF THE PARTIES TO A JOINT RESEARCH AGREEMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1) Field of Invention

The invention is in the general field of gas analysis. In particular it relates to the determination of the dew point of gases as well as detection and analysis of the components of gases.

2) Background

Dew point measurement of various compounds under different pressure regimes is an essential need in a number of applications. Since dew point corresponds to the vapor pressure of a given compounds at a given pressure, dew points are also routinely used as a measure of concentration of a material is gas phase.

The most common dew point measurement is used with water. The dew point of water is used in measured in many industrial applications. Both the raw dew point and the concentration inferred from the dew point are essential control parameters in many applications. For example water dew point, and the related partial vapor pressure, is needed in the semiconductor industry, the natural gas processing and transmission industry, air-dryer industry, and generally any process where the concentration of water needs to be measured.

However, dew point measurements are also needed and measured for many other compounds. For example in natural gas processing and transmission, hydrocarbon dew point of the gas stream needs to be determined for safety considerations as well as determining the value of the gas.

The most common method that has been used for many years for measuring the dew point is a chilled-mirror system. In this system, a mirror is chilled, and the surfaced is monitored to detect traces of condensation. The temperature at which condensation takes place is the dew point.

The detection was originally done by visual observation. This gave rise to errors emanating from human error and variability associated with operator skill.

More recently various means of automatic detection of the condensation have been described in prior art. One of the most commonly used methods involved shining a light beam, sometimes a laser beam, at the surface and monitoring for changes in the reflected beam as evidence of condensation on the surface (U.S. Pat. No. 5,028,143; U.S. Pat. No. 4,946,288; U.S. Pat. No. 4,799,235; U.S. Pat. No. 5,482,371). This method also suffers from a number of shortcomings. One of the shortcomings is that in the early stages of the condensation process, the changes in the reflected beam are not significant enough to indicate the exact dew point. The other shortcoming, encountered when there are various condensable vapors in the stream is that it is not clear what has been condensed on the surface first. For example, when the gas to be measured contains hydrocarbons and water at unknown quantities, either one may condense first depending on their relative vapor pressure and the total pressure and the temperature of the mirror. The changes in the reflected beam, typically cannot distinguish the substance that has been condensed. Another shortcoming is that these mirrors, typically made of metal, will be contaminated and degrade over times and their characteristics and thus their reflectance properties will change. A further problem is that the light beam actually has to travel through some of the gas before it hits the mirror and before it hits the detectors. This requirement makes the setup harder to implement.

There are other, non-optical methods described for detection of dew formation. Prior art described detection of dew formation by ultrasonic means (U.S. Pat. No. 6,327,890), MEM based devices (U.S. Pat. No. 6,126,311), measuring heat flow to the surface (U.S. Pat. No. 5,165,793), impedance changes (U.S. Pat. No. 4,948,263). None of these methods can determine the nature of the condensate accurately and also have reliability issues.

BRIEF SUMMARY OF THE INVENTION

The present invention allows for accurate determination of the dew point of any mixture of gases as well as identifying the chemical nature of the condensate. It also allows for identification of trace components in a gas stream whose concentrations are too low in the gas phase to be measured. The invention uses an optical element whose surface is exposed to a gas while it is cooled and light undergoes total internal reflection inside. The light hits the surfaces from underneath the surfaces which are exposed to the gas. Upon condensation of any component of the gas, the spectral content of the light changes due to the condensate on the surface of the optical element. Measurement of the spectral content of the returning light, along with measurement of the temperature of the surface of the optical element as well as the gas pressure allows the determination of the dew point, as well as the identification of the condensate and its concentration in the analyzed gas.

BRIEF DESCRIPTION OF THE SEVERAL VIEWS OF THE DRAWING

FIG. (1)—An exemplary schematic of the invention. The seal separates the process gas to be analyzed from the instrument. The cooling element could be a thermoelectric element or could be a heat conductor connected to a cooling source. The number of internal bounces can vary from 1 to many. As condensation builds on the optical element, the optical signal is attenuated depending on the chemical nature of the condensate. A temperature sensor measures the temperature at which condensation occurs. A pressure sensor provides the gas pressure.

FIG. (2)—Another exemplary implementation of the invention. The optical signal goes through many bounces internally and exits the other side where it will be analyzed spectrally. An exemplary ray of the optical signal is shown.

FIG. (3)—This configuration is similar to the configuration shown in FIG. (2) except that the optical signal enters and exits the same side of the optical element. An exemplary ray of the optical signal is shown.

DETAILED DESCRIPTION OF THE INVENTION

Figure 1:
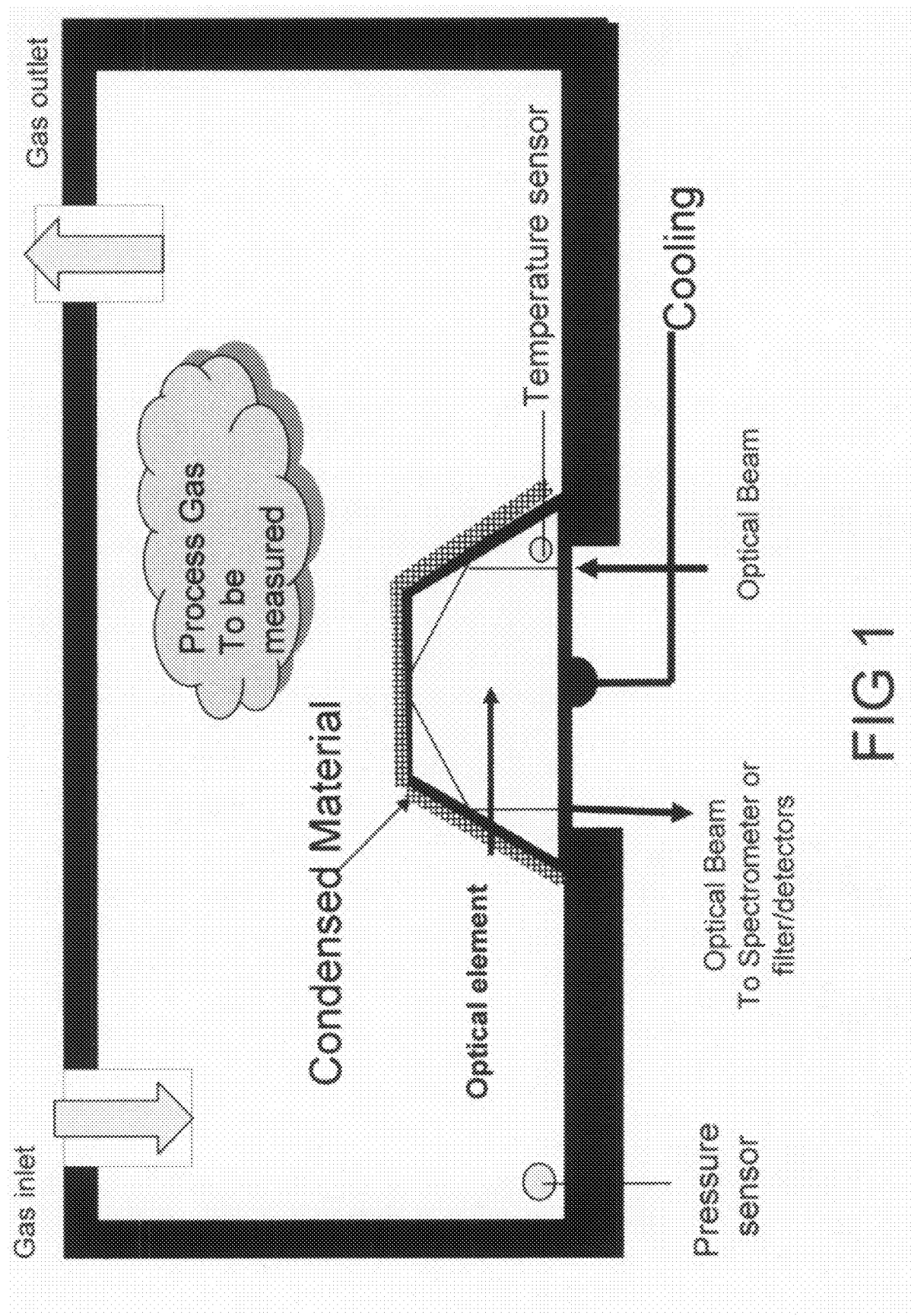
Figure 2:
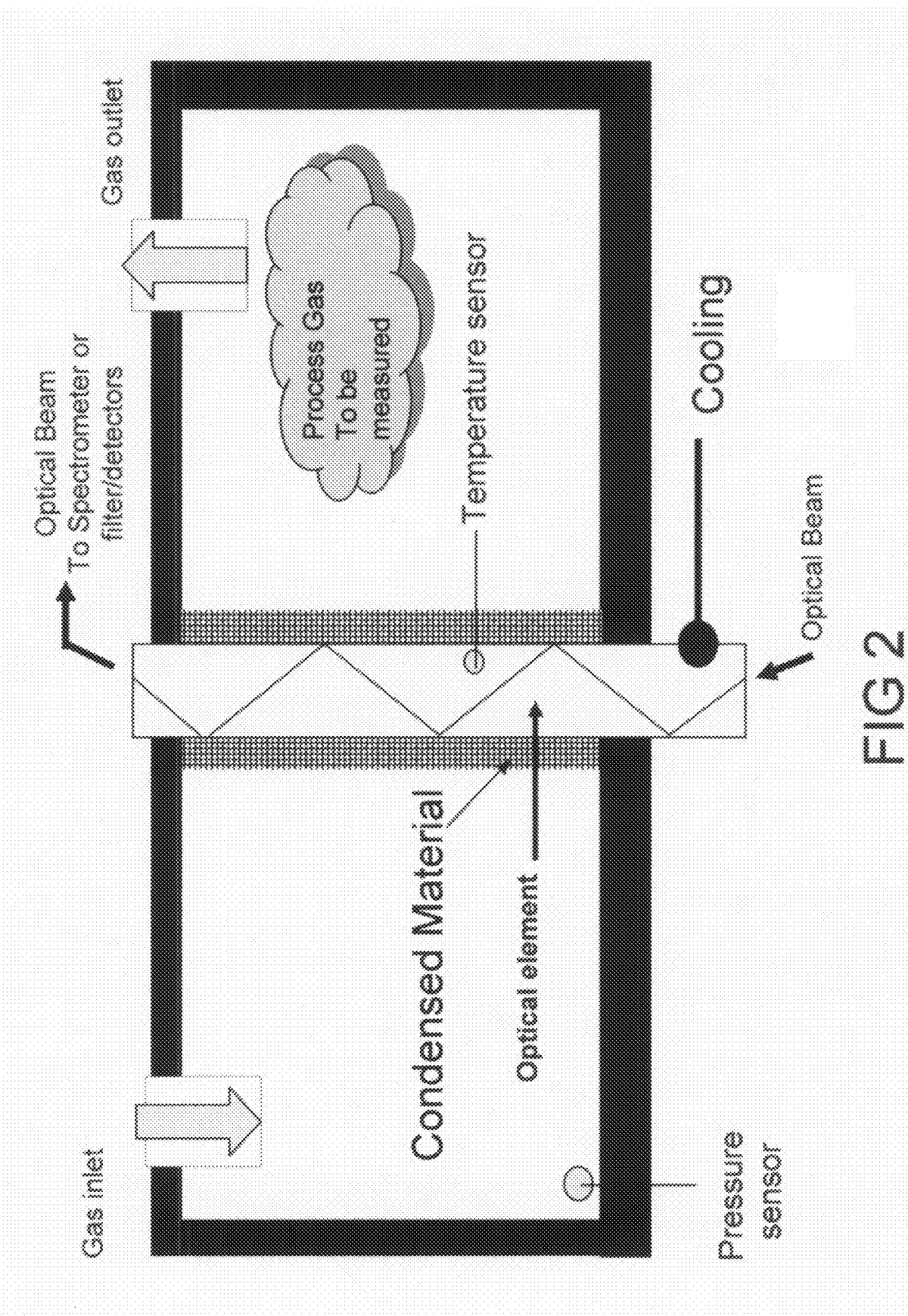
Figure 3:
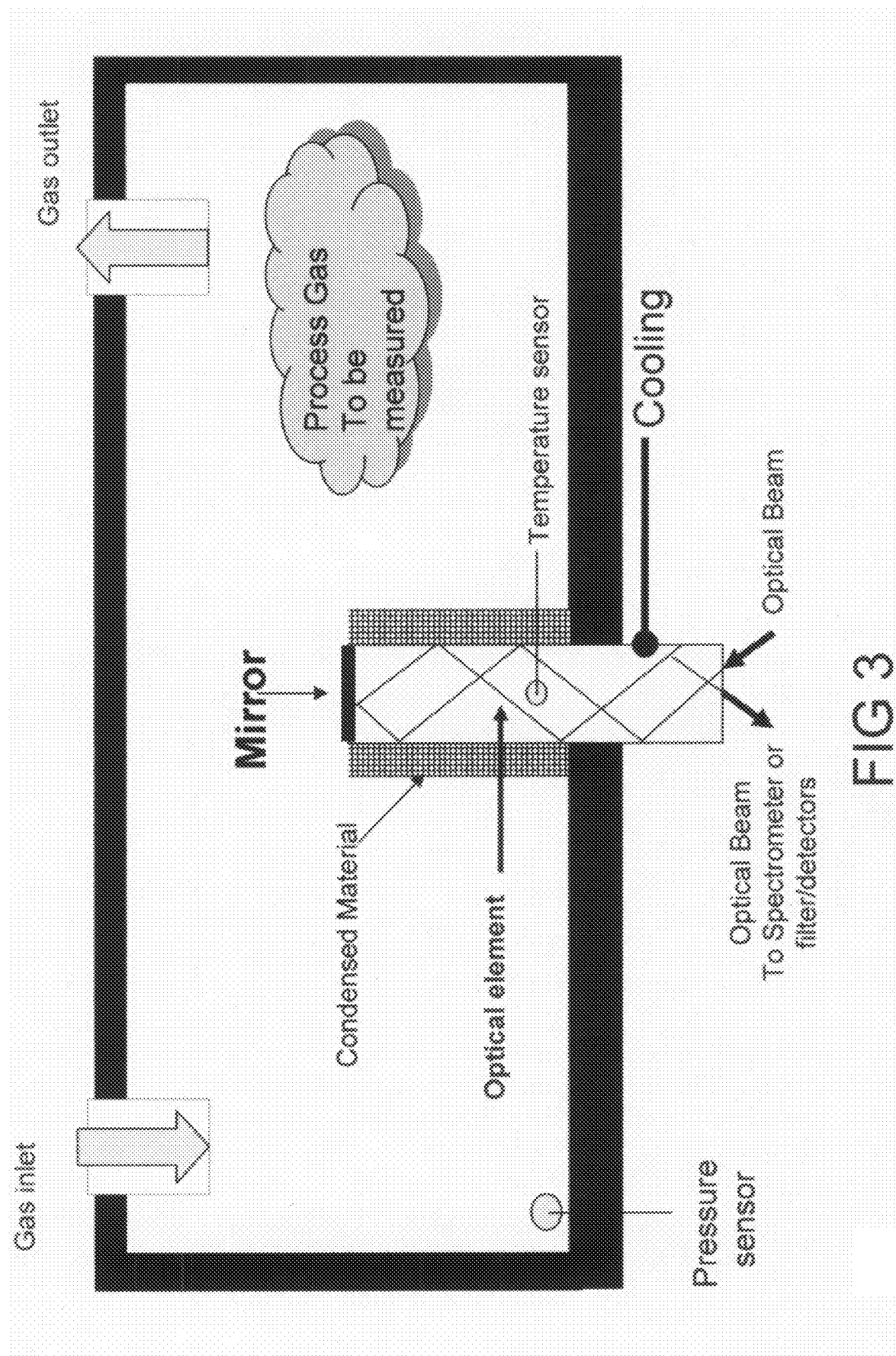

This invention addresses many of these shortcomings. A possible configuration is shown in FIG. 1, although many other configurations are also possible.

In the present invention, we expose the surface of an optical element to the gas stream whose dew point needs to be measured. The optical element is cooled while monitoring its surface temperature, until condensation takes place as shown in FIG. (2). The reflected beam which has gone under total internal reflection is monitored spectrally. This can be achieved by directing the reflected beam into a traditional spectrometer, or by using one or more optical filters in combination with detectors to monitor specific spectral lines corresponding to the material of interest.

As the optical element is cooled, at some temperature, there will be condensation on the surface of the said optical element exposed to the gas stream. Because the evanescent wave of the electrical field, resulting from the optical beam used, penetrates the material condensed on the surface, there will be optical absorption in certain spectral regions, characteristic of the condensed material. This optical absorption can be used as an indication of condensation. This is achieved by monitoring the reflected optical radiation in specific spectral regions of interest.

As an example, we describe the measurement of hydrocarbon dew points in the natural gas production, storage, and transmission. The hydrocarbon dew point is an important parameter that needs to be determined. The current invention can be used for in this application. The surface of the optical element is exposed to the gas stream while being cooled. The reflected beam is monitored at wavelengths corresponding to hydrocarbon absorption. Although many different wavelengths could be monitored, a particular wavelength of interest, where all hydrocarbons absorb strongly is around the 3.1-3.5 $\mu m$ region. If we monitor this spectral region as well as wavelength corresponding to the optical absorption of water (such the ~2.8 $\mu m$) or alcohols, we can see a change in the signal of one or several of these spectral regions, as condensation takes place. The change in the intensity of any of these spectral regions corresponds to the presence of the corresponding material on the surface of the chilled optical element. Additional spectral regions can be monitored for potential condensation by vapors which will absorb radiation in those regions. For example, the region around 10 $\mu m$, corresponding to the C—O bonds, can be monitored. Absorption in this region signals presence of compounds with C—O bond, such as alcohols. As methanol is also a contaminant in natural gas, monitoring in this region can be used for detection of condensate that has methanol in it.

Alternatively, the reflected signal can be taken to a spectrometer with a spectral region of interest. Then the presence of many different compounds in the condensate can be monitored at the same time. The spectral regions of interest are typically from 1.8 $\mu m$ to 12 $\mu m$, because this spectral area has absorption lines that indicate the composition of most condensates. Although in general any spectral region, even in the <1.5 $\mu m$ region can be monitored of spectral signatures corresponding to potential condensate material exist in that region.

Although the material of the optical element is not critical to the method described in this invention, it would be helpful if it is substantially transparent in the spectral regions that the reflected beam is to be monitored. Since the Infrared spectral region exhibits very strong absorption for many molecules and also exhibits rich spectral features for most molecules, materials that are somewhat transparent in the Infrared spectral region are particularly useful as the optical element in this invention.

It is also helpful if the material has a high coefficient of thermal conductivity. The higher the thermal conductivity of the optical element, the faster it can be cooled down, and the faster the measurement can be made.

A different implementation of the same principle is possible where one can use a bare, unclad optical fiber as the optical element to be chilled. Since optical signal propagates through an optical fiber by going through many internal reflections, the optical power will be attenuated if there is any material condensed on that fiber. By bending the fiber the angle of incidence can be increased where and the electrical field due to the optical signal will penetrate through the optical fiber more than if the optical fiber was straight. Now if the optical fiber is chilled by any means, vapor can condense on it and the presence of condensate can be detected as described above. The optical fiber can be chilled by placing it in contact with a chilled element.

As another example, we can discuss the determination of water dew point, and thus its partial vapor pressure in streams of dry gases. Determination of water content is particularly important in gases used in the semiconductor industry, as water is one of the main and important contaminants in these gases that adversely effect the production of semiconductor chips. In this application, the ATR surface is again exposed to the gas stream and cooled while monitoring the temperature, pressure, and the intensity of the reflected beam at one of the wavelengths that are characteristic of water absorption. Many such wavelength exist, and the choice depends on absorption by other potential contaminants.

The advantage of using this method for determination of water vapor or other gases is that there is a very wide dynamic range which is the function of the cooling power. Therefore, the dynamic range is provided by the range of the cooling power provided and not be the optics or optical signal power.

Another important application of this invention is construction of the phase diagram for a given gas. By using a pump or piston to change the pressure of the sample gas, the dew point at several pressures can be measured and spectral information regarding the liquid condensate gathered. By putting this information together, one can construct the phase diagram for the process gas. By having the spectral information on the condensate, one can gain information about what components of the process gas condensed at each pressure. This information is important in many applications.

A further utility of this invention is the analysis of condensable components in a gas mixture, particularly when the concentration of the condensable components is too low to be detected in the gas phase. The optical absorption of the liquid phase is much stronger than the gas phase for almost all materials. The reason is the much higher density of the liquid phase compared to the gas phase. By condensing the components of the gas into the liquid phase, the optical absorption becomes high enough to be detected easier than in the gas phase.

An application of the utility is analysis of breath. The most dominant ingredients of human breath are carbon dioxide and water vapor. However in addition to these components, based on physiological and dietary factors, many other organic compounds are found in the human breath. Detection of the presence and quantity of these components can lead to detection of different diseases, possible drug or alcohol intake, as well as providing information on the physiology of the subject. This invention allows the detection of these compounds by turning them into the liquid phase first. One may have to reduce the amount of water vapor or other abundant constituents from the breath stream first to reduce its dew point below that of component of interest.

It should be added that the present invention can also be used in a Raman setup.

What is claimed is:

1. An apparatus for measuring dew point of gases using spectral measurement or recognition of condensate, said apparatus comprising:
    an optical element, exposed to a gas or mixture of gasses;
    a cooling element to cool down said optical element to condensate one or more of said gas or mixture of gasses on a surface of said optical element,
    wherein an electromagnetic radiation hits said optical element in an angle that said electromagnetic radiation undergoes one or more total internal reflection in said optical element;
    a temperature measurement device to measure temperature of said optical element; and
    a pressure measurement device to measure pressure of said gas or mixture of gasses.

2. The apparatus as recited in claim 1, further comprising a heating element to evaporate condensation of said one or more of said gas or mixture of gasses on said surface of said optical element.

3. The apparatus as recited in claim 1, further comprising a spectrometer for measuring spectral content of said electromagnetic radiation undergone one or more total internal reflection in said optical element.

4. The apparatus as recited in claim 1, further comprising one or more optical filters and one or more detectors for measuring one or more peaks of spectral content of said electromagnetic radiation undergone one or more total internal reflection in said optical element.

5. The apparatus as recited in claim 1, wherein said optical element is an optical fiber without cladding.

6. The apparatus as recited in claim 5, wherein said temperature measurement device measures temperature using a Fiber-Bragg Grating written onto said optical fiber.

7. The apparatus as recited in claim 1, wherein said optical element comprises one or more of following material: sapphire, Zirconium Oxide, Zinc Selenide, Zinc sulfide, Silicon, glass, chalcogenide, diamond, or Germanium, with or without an optical or mechanical coating.

8. The apparatus as recited in claim 1, wherein said electromagnetic radiation is generated by a tungsten lamp.

9. The apparatus as recited in claim 1, wherein said electromagnetic radiation is generated by one or more fixed wavelength or tunable wavelength diodes or lasers.

10. The apparatus as recited in claim 1, wherein said electromagnetic radiation covers spectral region of 1.5 µm to 12 µm.

11. The apparatus as recited in claim 4, wherein said one or more optical filters comprise a band-pass filter, with band-pass anywhere between 3.0 µm and 3.5 µm, to indicate presence of a hydrocarbon in said condensate of said one or more of said gas or mixture of gasses on said surface of said optical element.

12. The apparatus as recited in claim 4, wherein said one or more optical filters comprise a band-pass filter, with band-pass anywhere between 1.8 µm and 2.3 µm or between 2.6 µm and 3.0 µm, to indicate presence of water in said condensate of said one or more of said gas or mixture of gasses on said surface of said optical element.

13. The apparatus as recited in claim 4, wherein said one or more optical filters comprise a band-pass filter, with band-pass anywhere between 9.8 µm and 10.5 µm, to indicate presence of alcohol in said condensate of said one or more of said gas or mixture of gasses on said surface of said optical element.

14. The apparatus as recited in claim 4, wherein said one or more optical filters and one or more detectors comprise a gradient optical filter in combination with a diode-array detector.

15. The apparatus as recited in claim 3, wherein said spectrometer is a FTIR.

16. The apparatus as recited in claim 1, wherein dew point is measured at several different pressures to construct a phase diagram with spectral information about said condensate for said dew point at different pressure values.

17. The apparatus as recited in claim 1, wherein said optical element is in contact with a cooled metal surface.

18. The apparatus as recited in claim 1, wherein said cooling element comprises a heat-pipe or coil.

19. The apparatus as recited in claim 1, further comprising a Raman spectrometer.

20. The apparatus as recited in claim 1, wherein said electromagnetic radiation is in infra-red range.

21. The apparatus as recited in claim 1, further comprising a material with a high thermal conductivity.

22. The apparatus as recited in claim 1, further comprising a bent optical fiber.

23. The apparatus as recited in claim 1, further comprising a pump.

24. The apparatus as recited in claim 1, further comprising a device to adjust pressure.

25. The apparatus as recited in claim 1, further comprising a device to measure or determine physiological or dietary factors.

26. The apparatus as recited in claim 1, wherein said electromagnetic radiation does not travel through said gas or mixture of gasses, when undergone one or more total internal reflection in said optical element.

27. The apparatus as recited in claim 1, further comprising a mirror.

28. The apparatus as recited in claim 1, wherein said electromagnetic radiation covers spectral region of 0.4 µm to 1.5 µm.

29. An optical element which is exposed to a quantity of gas, and the said optical element is cooled, leading to the condensation of liquid on its surfaces, and where an optical signal enters the said optical element, and is incident upon the internal surface of the said optical element at an angle which causes the optical signal to undergoing total internal reflection in the optical element, one or several times, and then exits the optical element where its spectral content is measured using a spectrometer, or one or several optical filters in combination with detectors, and where the temperature of the surface where condensation takes place is monitored by temperature sensing devices, the pressure of the gas is monitored using pressure sensing devices, and the element is periodically cooled and heated to cause condensation and then evaporation of condensate.

* * * * *